(12) United States Patent
Mou et al.

(10) Patent No.: US 11,530,970 B2
(45) Date of Patent: Dec. 20, 2022

(54) PARTICLE DETECTING DEVICE

(71) Applicant: Microjet Technology Co., Ltd., Hsinchu (TW)

(72) Inventors: Hao-Jan Mou, Hsinchu (TW); Ching-Sung Lin, Hsinchu (TW); Chin-Chuan Wu, Hsinchu (TW); Chi-Feng Huang, Hsinchu (TW); Yung-Lung Han, Hsinchu (TW); Chang-Yen Tsai, Hsinchu (TW); Wei-Ming Lee, Hsinchu (TW)

(73) Assignee: Microjet Technology Co., Ltd., Hsinchu (TW)

( * ) Notice: Subject to any disclaimer, the term of this patent is extended or adjusted under 35 U.S.C. 154(b) by 0 days.

(21) Appl. No.: 17/368,297

(22) Filed: Jul. 6, 2021

(65) Prior Publication Data
US 2022/0034779 A1 Feb. 3, 2022

(30) Foreign Application Priority Data
Jul. 31, 2020 (TW) .................................. 109126114

(51) Int. Cl.
*G01N 15/06* (2006.01)
(52) U.S. Cl.
CPC ................. *G01N 15/0656* (2013.01)

(58) Field of Classification Search
CPC ............ G01N 15/0656; G01N 1/2273; G01N 33/0011; G01N 15/0266; G01N 2015/0046; G01N 15/0606
See application file for complete search history.

(56) References Cited

U.S. PATENT DOCUMENTS

| 2014/0083167 A1* | 3/2014 | Liu ......................... G01N 15/06 73/28.02 |
| 2018/0120248 A1* | 5/2018 | Akuzawa ............... G01N 27/22 |
| 2019/0064104 A1 | 2/2019 | Mou et al. |
| 2021/0123849 A1* | 4/2021 | Singh .................. H01L 41/1132 |
| 2021/0405007 A1* | 12/2021 | Solomon .................. G01G 3/13 |

FOREIGN PATENT DOCUMENTS

| CN | 103698258 A | 4/2014 |
| TW | M575861 U | 3/2019 |
| TW | 201945710 A | 12/2019 |
| TW | I696818 B | 6/2020 |

* cited by examiner

*Primary Examiner* — David Z Huang
(74) *Attorney, Agent, or Firm* — Birch, Stewart, Kolasch & Birch, LLP

(57) ABSTRACT

A particle detecting device is provided. The particle detecting device includes a resonator and a piezoelectric actuator. The piezoelectric actuator is used to transport a gas into the resonator, and a mass and a concentration of the screened and required-diameter particles are detected through the resonator. Thus, the air quality can be monitored immediately anytime and anywhere.

9 Claims, 22 Drawing Sheets

PARTICLE DETECTING DEVICE

FIELD OF THE INVENTION

The present disclosure relates to a particle detecting device, and more particularly to a particle detecting device easy to carry and capable of monitoring air quality immediately anytime and anywhere.

BACKGROUND OF THE INVENTION

Nowadays, people pay more and more attention to the air quality in the environment. Various of gases and substances, such as carbon monoxide, carbon dioxide, volatile organic compounds (VOC), Particulate Matter 2.5 (PM2.5), nitric oxide, sulfur monoxide, and so on, exposure in the ambient environment will cause human health problems or even is harmful to the life. Therefore, people pay more and more attention to the air quality in the environment in every country, and how to monitor and keep away from the harmful air quality become a currently concerned issue.

Generally, it is feasible to use a particle detecting device to monitor the air quality in the environment. If the particle detecting device is capable of providing people with the monitored information relating to the environment immediately for warning, it may help people to escape or prevent from the injuries and influence on human health caused by the exposure to the gases and substances described above in the ambient environment. In other words, the particle detecting device is suitable for monitoring the air in the ambient environment may be a portable miniature device easy to carry, and can monitor the air quality immediately everywhere and anytime, which are main subjects of research and development in the present disclosure.

SUMMARY OF THE INVENTION

An object of the present disclosure is to provide a particle detecting device. A portable miniature particle detecting device is formed by a resonator and a piezoelectric actuator. The piezoelectric actuator is used to transport a gas into the resonator, and detects a mass and a concentration of the screened and required-diameter particles through the resonator. Thus, the air quality can be monitored immediately anytime and anywhere, and people are allowed to understand the gas quality of the inhaled gas.

In accordance with an aspect of the present disclosure, a particle detecting device is provided. The particle detecting device includes a resonator and a piezoelectric actuator. The resonator includes a box, a driving board, a piezoelectric vibrator and a suspended-particle sensor. The box includes a sampling chamber, an air inlet and a waterproof and breathable membrane. The air inlet is covered and attached by the waterproof and breathable membrane. The waterproof and breathable membrane is for blocking large particles with a particle size large than or equal to a threshold diameter contained in an external gas, therefore the gas outside the particle detecting device is inhaled into the sampling chamber through the air inlet. The driving board is disposed on a bottom of the sampling chamber and comprises at least one passage hole disposed thereon. The piezoelectric vibrator is packaged on the driving board. The suspended-particle sensor is packaged on the piezoelectric vibrator. Moreover, the suspended-particle sensor is in correspondence with the air inlet and maintains a spacing distance. Driving power and operation frequency are provided to the piezoelectric vibrator by the driving board, a resonance frequency of the piezoelectric vibrator is change, and the screened and required-diameter particles are sedimented and collected on a surface of the suspended-particle sensor, so that a mass and a concentration of the screened and required-diameter particles can be detected. The piezoelectric actuator is sealed and connected to one side of the resonator, so that the external gas is inhaled into the sampling chamber through the air inlet, passed by the suspended-particle sensor, and discharged out of the particle detecting device through the at least one passage hole and the piezoelectric actuator in sequence.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

Figure 1:
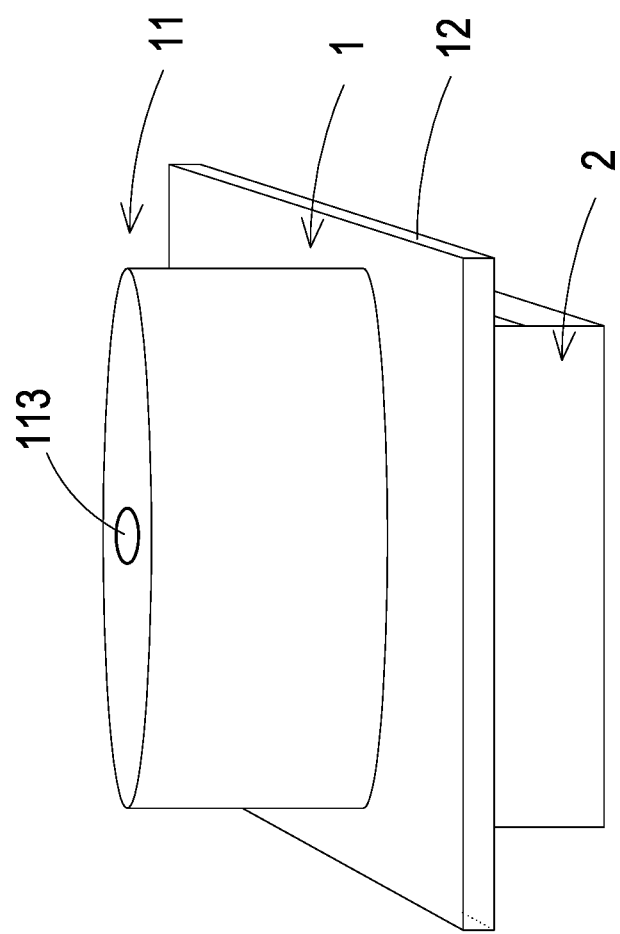
FIG. 1 is a schematic exterior view illustrating a particle detecting device according to an embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

As shown in FIG. 1 and FIGS. 2A to 2D, the present disclosure provides a particle detecting device including a resonator 1 and a piezoelectric actuator 2. The resonator 1 includes a box 11, a driving board 12, a piezoelectric vibrator 13 and a suspended-particle sensor 14. The box 11 comprises a sampling chamber 111, an air inlet 112 and a waterproof and breathable membrane 113, and the air inlet 112 is covered and attached by the waterproof and breathable membrane 113. The sampling chamber 111 is in fluid communication with the air inlet 112, and the driving board 12 is disposed in the sampling chamber 111. In the embodiment, the waterproof and breathable membrane 113 blocks large particles with a particle size large than or equal to a threshold diameter contained in an external gas. When the external gas is inhaled into the sampling chamber 111 through the air inlet 112, therefore only the screened and required-diameter particles with particle size smaller than the threshold diameter can pass through the waterproof and breathable membrane 113 and be inhaled into the sampling chamber 111. In this embodiment, the threshold diameter is 10 μm, but not limited thereto.

Moreover, the driving board 12 is disposed on bottom of the sampling chamber 111 and comprises at least one passage hole 121 disposed thereon. The piezoelectric vibrator 13 is packaged on the driving board 12, and the suspended-particle sensor 14 is packaged on the piezoelectric vibrator 13. The suspended-particle sensor 14 is corresponding in position to the air inlet 112 and maintains a spacing distance. In that, the driving board 12 provides driving power and operation frequency to the piezoelectric vibrator 13 and changes the resonance frequency of the piezoelectric vibrator 13, and the screened and required-diameter particles are sedimented and collected on a surface of the suspended-particle sensor 14. Thus, the suspended-particle sensor 14 can detect a mass and a concentration of the screened and required-diameter particles through the correlation between the changes of inherent frequency and the changes of particle mass. Certainly, the gas transportation in the inner chambers, such as the sampling chamber 111 of the resonator 1, is achieved by the piezoelectric actuator 2. In the embodiment, the piezoelectric actuator 2 is disposed on, sealed and connected to one side of the resonator 1. When the piezoelectric actuator 2 is driven to enable the gas transportation, the external gas is inhaled into the sampling chamber 111 through the air inlet 112. Thereafter, the particles contained in the gas are sedimented and collected by the suspended-particle sensor 14 according to the resonance frequency change of the resonator 1, so as to measure the mass, the particle size, and the concentration of the particles contained in the gas. Moreover, the inhaled gas is led out of the resonator 1 through the at least one passage hole 121 of the driving board 12, and further discharged out of the particle detecting device by the piezoelectric actuator 2.

In the embodiment, the piezoelectric vibrator 13 is a quartz chip, but not limited thereto. Preferably but not exclusively, the suspended-particle sensor 14 is a PM10 sensor, a PM2.5 sensor, or a PM1 sensor, but not limited thereto, so as to measure the mass, the particle size, and the concentration of the particles contained in the gas.

Figure 2A:
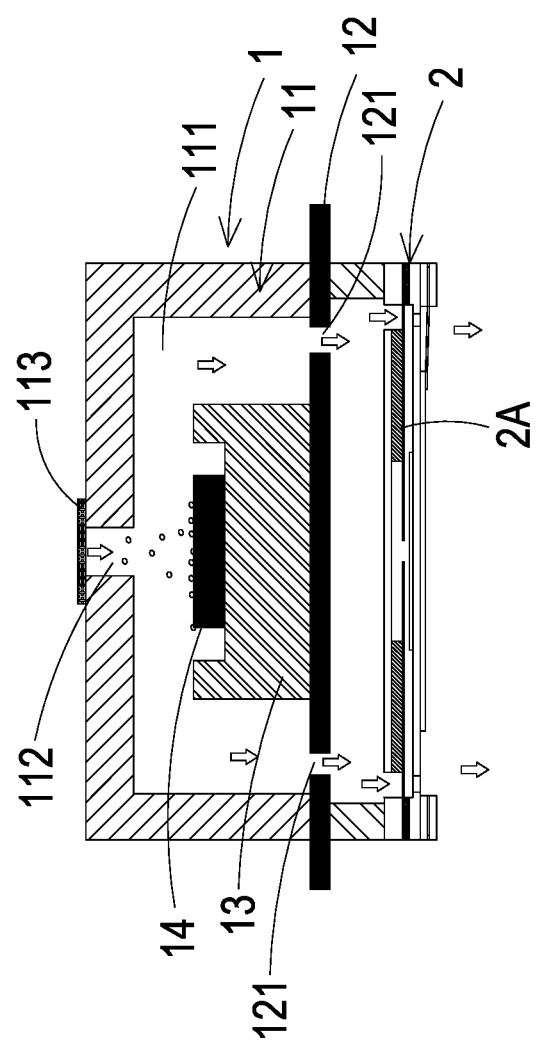
FIG. 2A is a cross sectional view illustrating a micro pump of the particle detecting device of the present disclosure for a gas transporting operation.
Figure 2B:
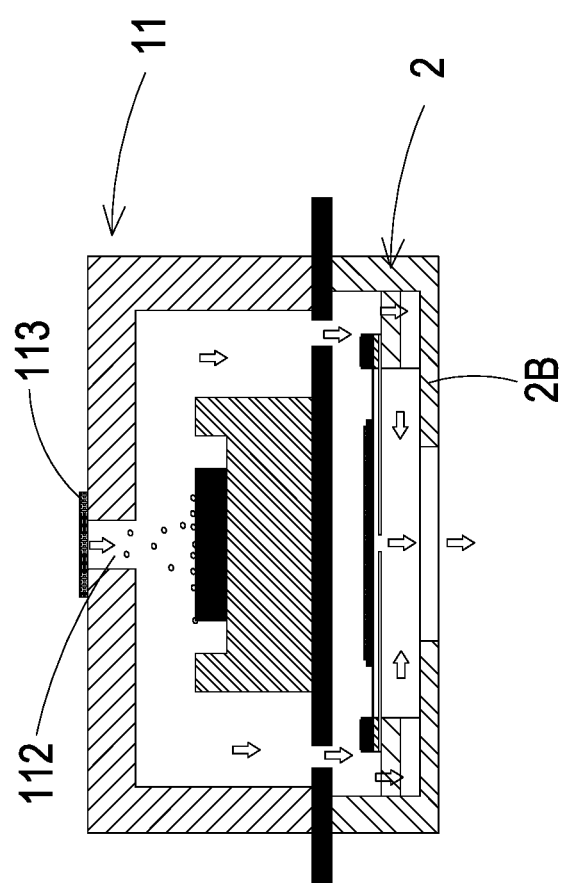
FIG. 2B is a cross sectional view illustrating a blower-type micro pump of the particle detecting device of the present disclosure for a gas transporting operation.
Figure 2C:
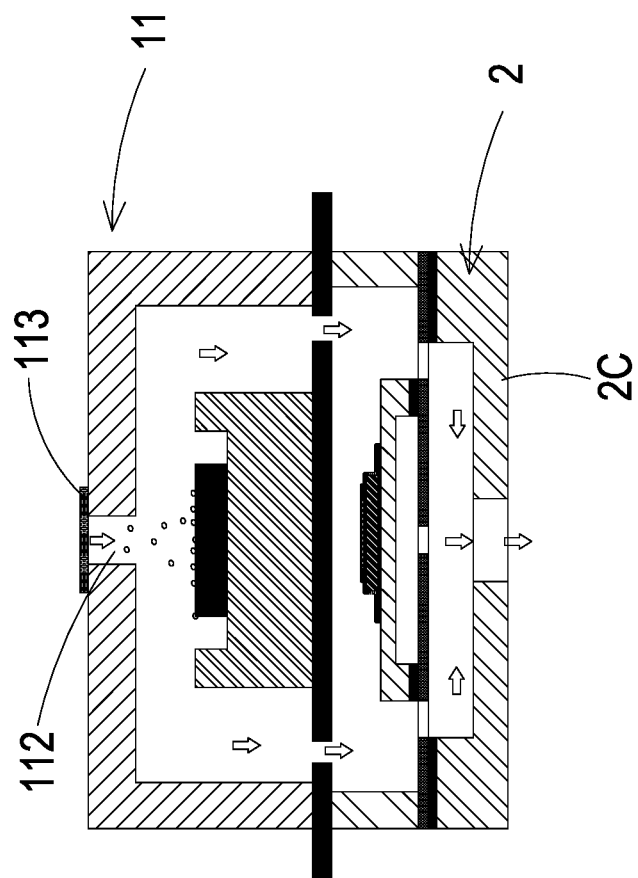
FIG. 2C is a cross sectional view illustrating a blower-type microelectromechanical-system micro pump of the particle detecting device of the present disclosure for a gas transporting operation.
Figure 2D:
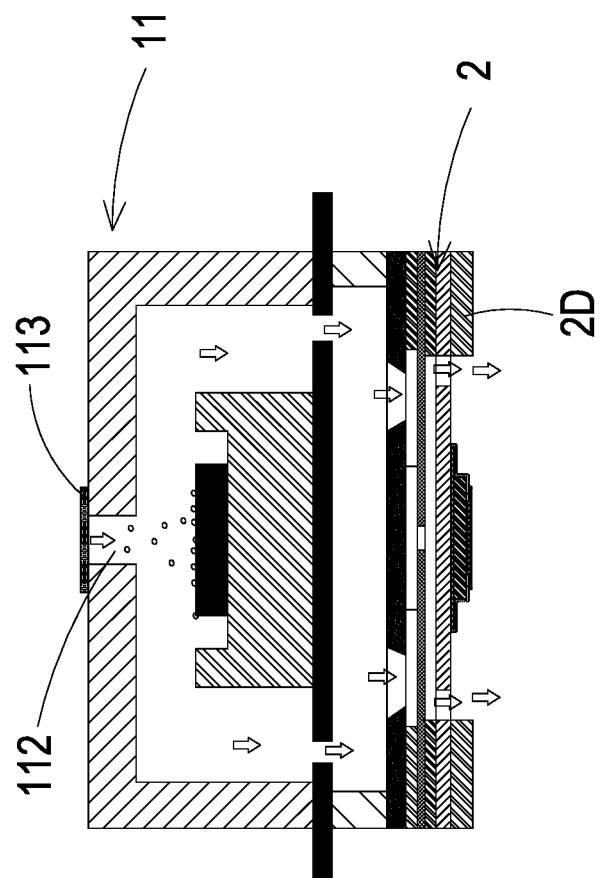
FIG. 2D is a cross sectional view illustrating a microelectromechanical-system pump of the particle detecting device of the present disclosure for a gas transporting operation.

In the embodiment, the piezoelectric actuator 2 can be various types of micro gas transportation structure, for example a micro pump 2A shown in FIG. 2A, a blower-type micro pump 2B shown in FIG. 2B, a blower-type microelectromechanical-system micro pump 2C shown in FIG. 2C, or a microelectromechanical-system pump 2D shown in FIG. 2D. As for the related structures and the gas transportation operation steps of the above mentioned micro pump 2A, the blower-type micro pump 2B, the blower-type microelectromechanical-system micro pump 2C and the microelectromechanical-system pump 2D are described below.

Figure 3A:
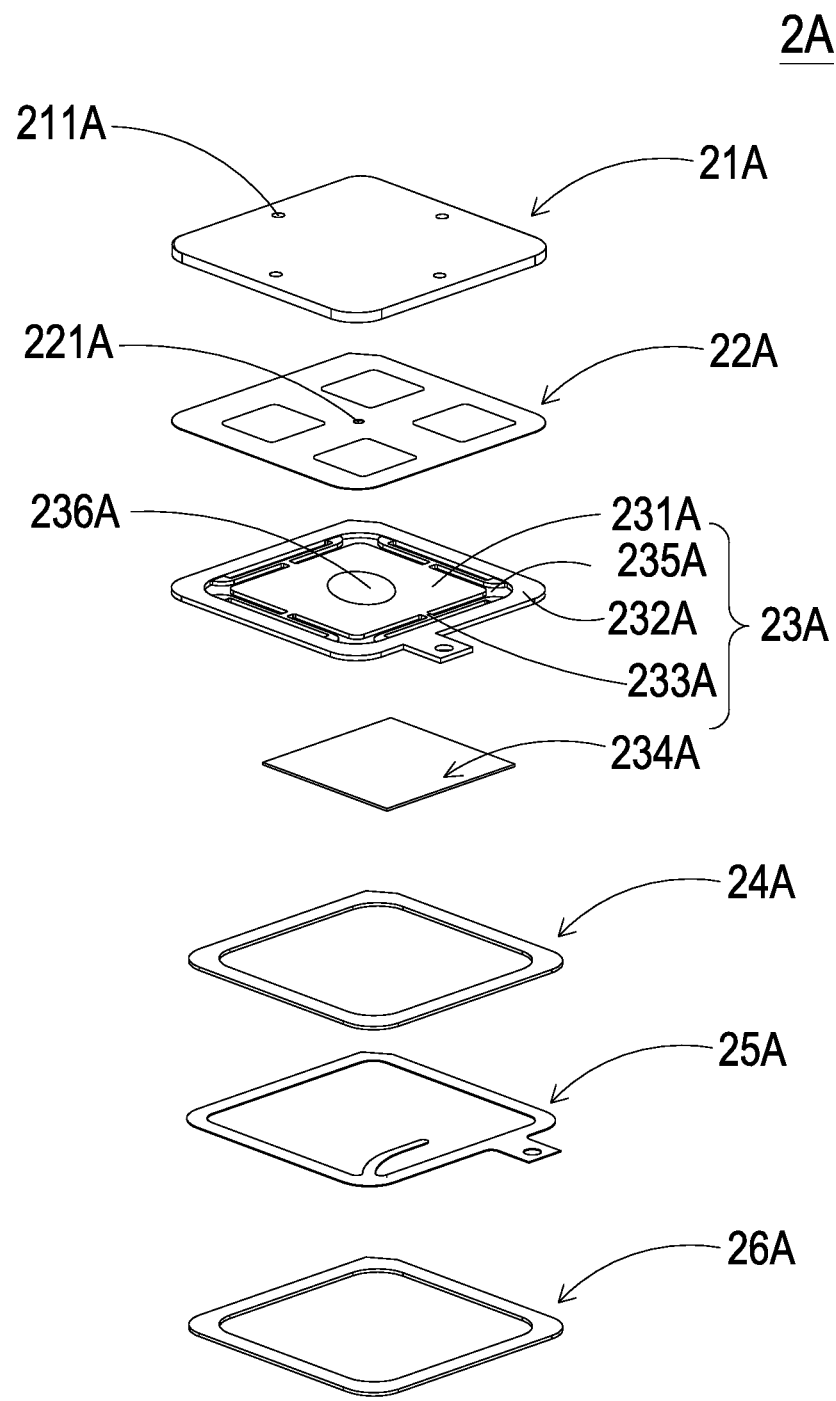
FIG. 3A is a schematic exploded view illustrating the micro pump of the particle detecting device of the present disclosure and taken along front viewpoint.
Figure 3B:
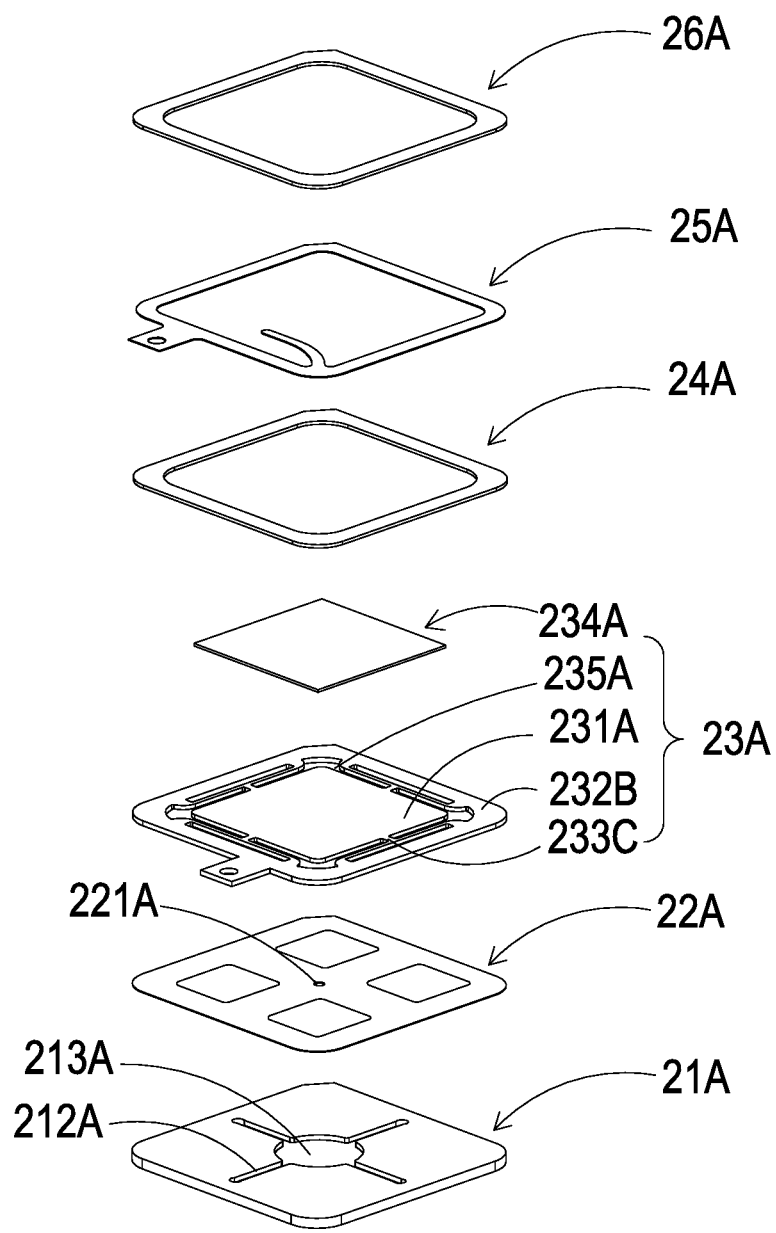
FIG. 3B is a schematic exploded view illustrating the micro pump of the particle detecting device of the present disclosure and taken along rear viewpoint.
Figure 4A:
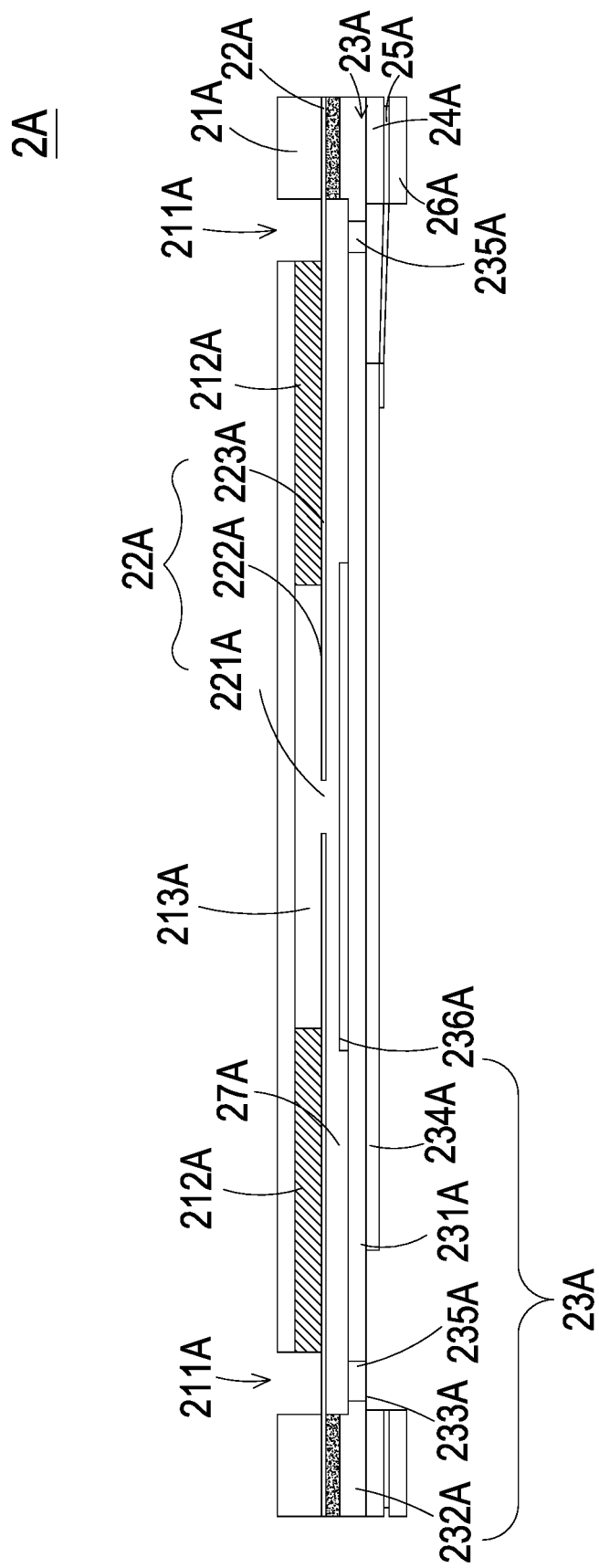
FIG. 4A is a schematic cross-sectional view illustrating the micro pump of particle detecting device of the present disclosure.

As shown in FIG. 3A, FIG. 3B and FIG. 4A, the micro pump 2A is formed by sequentially stacking an inlet plate 21A, a resonance plate 22A, a piezoelectric member 23A, a first insulation plate 24A, a conductive plate 25A and a second insulation plate 26A. In the embodiment, the inlet plate 21A includes at least one inlet aperture 211A, at least one convergence channel 212A and a convergence chamber 213A. The at least one inlet aperture 211A is disposed to inhale the gas. The inlet aperture 211A is disposed corresponding in position to the convergence channel 212A and in communication therewith. The convergence channel 312A converge to the convergence chamber 313A, so as to allow the gas inhaled from the inlet aperture 211A to converge to the convergence chamber 213A. In the embodiment, the number of the inlet apertures 211A and the number of the convergence channels 212A are the same. Preferably, the number of the inlet apertures 211A and the number of the convergence channels 212A are exemplified by four, but not limited thereto. The four inlet apertures 211A penetrate through the inlet plate 21A into the four convergence channels 22A respectively, and the four convergence channels 212A converge to the convergence chamber 213A. In the embodiment, the resonance plate 22A is attached to and assembled on the inlet plate 21A. The resonance plate 22A has a central aperture 221A, a movable part 222A and a fixed part 223A. The central aperture 221A is located at the center of the resonance plate 22A and is corresponding in position to the convergence chamber 213A of the inlet plate 21A. The movable part 222A is disposed at the region around the central aperture 221A and is corresponding to the convergence chamber 223A. The fixed part 223A is disposed at the region of the periphery of the resonance plate 22A and securely attached on the inlet plate 21A. In the embodiment, the piezoelectric member 23A is attached on the resonance plate 22A and is corresponding to the resonance plate 22A. The piezoelectric member 23A includes a suspension plate 231A, an outer frame 232A, at least one bracket 233A and a piezoelectric element 234A. The suspension plate 231A is square-shaped and permitted to undergo a bending deformation. The outer frame 232A is disposed around a periphery of the suspension plate 231A. The at least one bracket 233A is connected between the suspension plate 231A and the outer frame 232A for elastically supporting the suspension plate 231A. The piezoelectric element 234A is attached to a surface of the suspension plate 231A for driving the suspension plate 231A to undergo the bending deformation as a voltage is applied thereto. In the embodiment, at least one vacant space 235A is formed between the suspension plate 231A, the outer frame 232A and the at least one bracket 233A for allowing the gas to flow therethrough. In addition, a bulge 236A is formed on a surface of the suspension plate 231A, opposite to the surface that the suspension plate 231A attached. In that, the inlet plate 21A, the resonance plate 22A, the piezoelectric member 23A, the first insulation plate 24A, the conductive plate 25A and the second insulation plate 26A are stacked sequentially. In the embodiment, a chamber space 27A is formed between the suspension plate 231A of the piezoelectric member 23A and the resonance plate 22A. Moreover, the chamber space 27A can be formed by filling a gap between the resonance plate 22A and the outer frame 232A of the piezoelectric member 23A with a material, such as a conductive adhesive, but not limited thereto. Thus, a specific depth between the resonance plate 22A and the suspension plate 231A is maintained to allow the gas to pass rapidly. In addition, since the suspension plate 231A and the resonance plate 22A are maintained at a suitable distance, so that the contact interference therebetween is reduced and the generated noise is largely reduced.

Figure 4B:
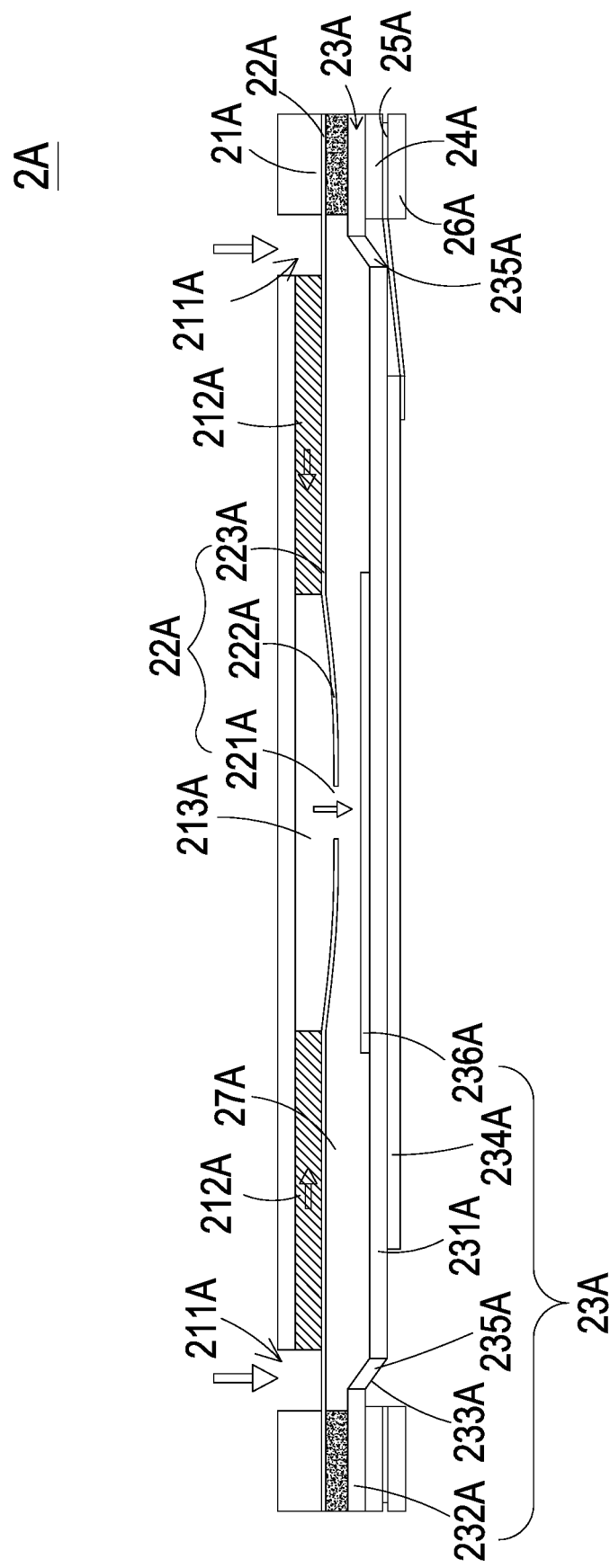
FIGS. 4B to 4D schematically illustrate the operation steps of the micro pump of FIG. 4A.
Figure 4C:
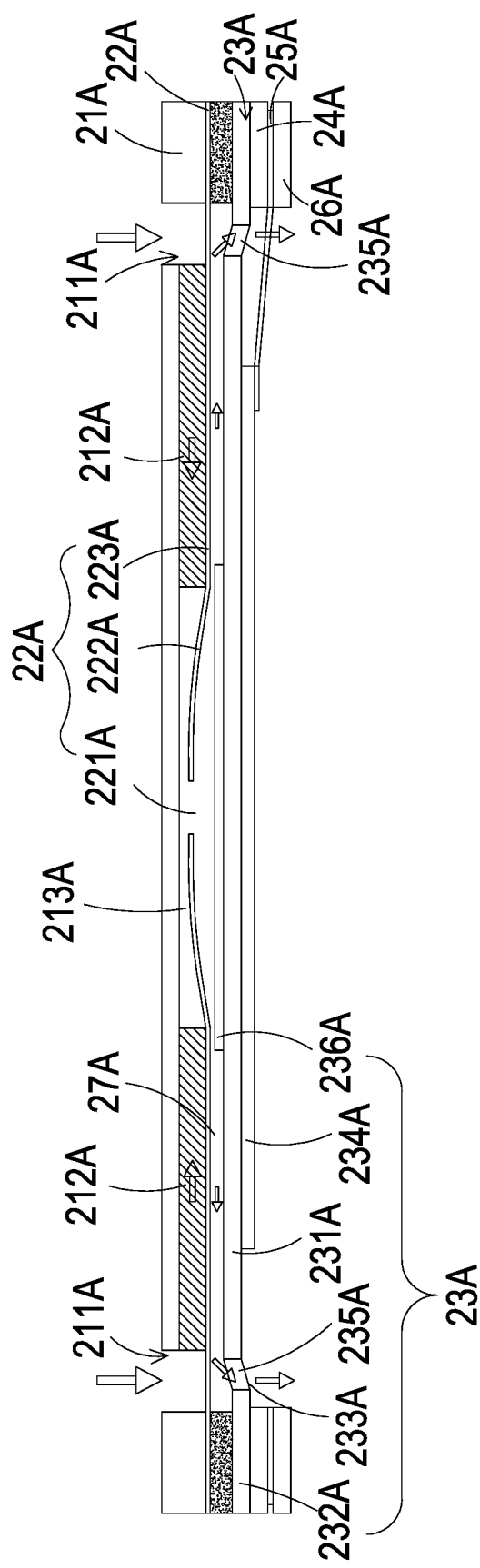
Figure 4D:
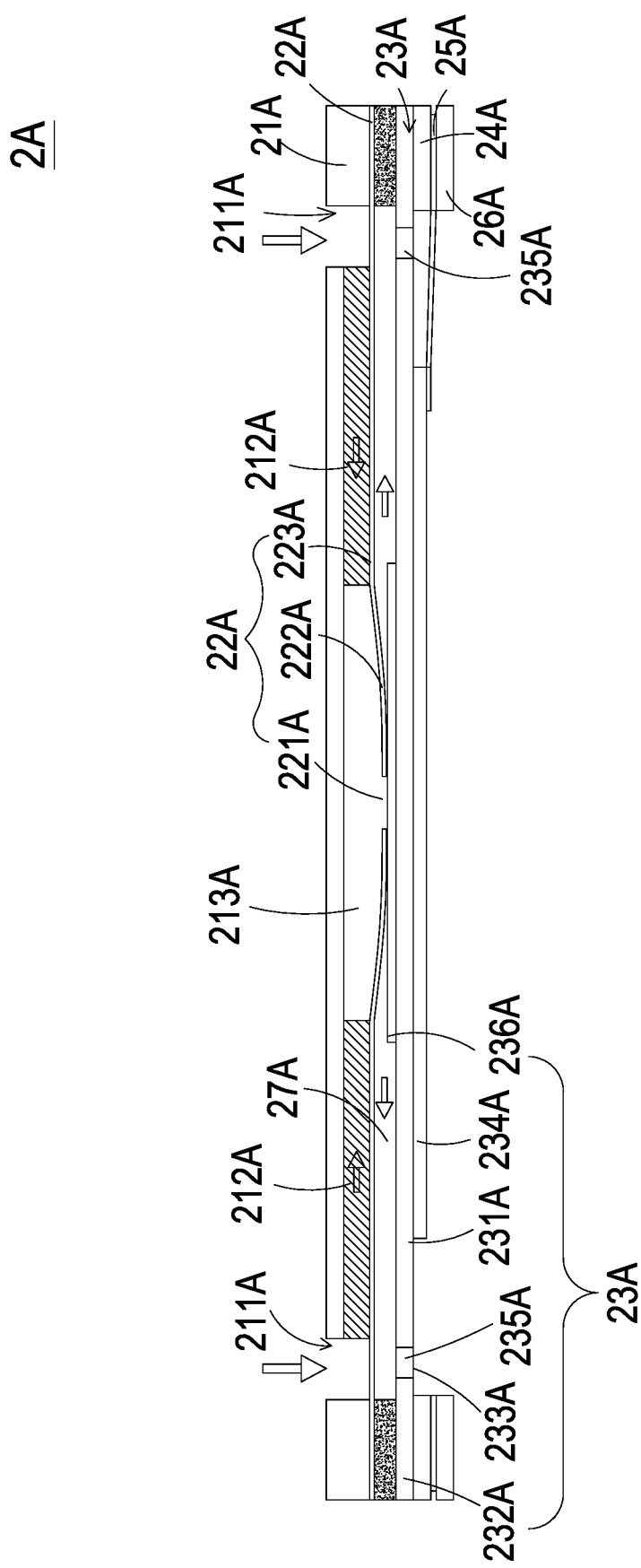

In order to understand the operation steps of the above-mentioned micro pump 2A for gas transportation, please refer to FIGS. 4B to 4D. Firstly, please refer to FIG. 4B. When the piezoelectric element 234A of the piezoelectric member 23A is deformed when a voltage is applied thereto, the suspension plate 231A is driven to displace downwardly. In that, the volume of the chamber space 27A is increased and e a negative pressure is generated in the chamber space 27A, and the gas in the convergence chamber 213A is introduced into the chamber space 27A. At the same time, the resonance plate 22A is in resonance with the suspension plate 231A and displaced synchronously. Thereby, the volume of the convergence chamber 213A is increased and the gas in the convergence chamber 213A is introduced into the chamber space 27A, thus a negative pressure is also generated in the convergence chamber 213A, and the gas is inhaled into the convergence chamber 213A through the inlet apertures 211A and the convergence channels 212A. Then, as shown in FIG. 4C, the piezoelectric element 234A drives the suspension plate 231A to displace upwardly and compress the chamber space 27A. Similarly, the resonance plate 22A is in resonance with the suspension plate 231A and is displaced upwardly. Thus, the gas in the chamber space 27A is further transported downwardly to pass through the vacant spaces 235A and achieves the effective gas transportation. Finally, as shown in FIG. 4D, when the suspension plate 231A return to an initial position, the resonance plate 22A is keep on displacing downwardly due to inertia. In that, the resonance plate 22A pushes the gas in the chamber space 27A toward the vacant spaces 235A, and the volume of the convergence chamber 213A is increased. Thus, the gas can continuously pass through the inlet apertures 211A and the convergence channels 212A, and converge into the convergence chamber 213A. By repeating the operation steps illustrated in FIGS. 4B to 4D continuously, the gas enters the inlet apertures 211A continuously, flows through a flow path formed by the inlet plate 21A and the resonance plate 22A and generates a pressure gradient, and then is transported downwardly through the vacant spaces 235A to transport the gas at high speed, and the gas transporting operation of the micro pump 2A is completed.

Figure 5A:
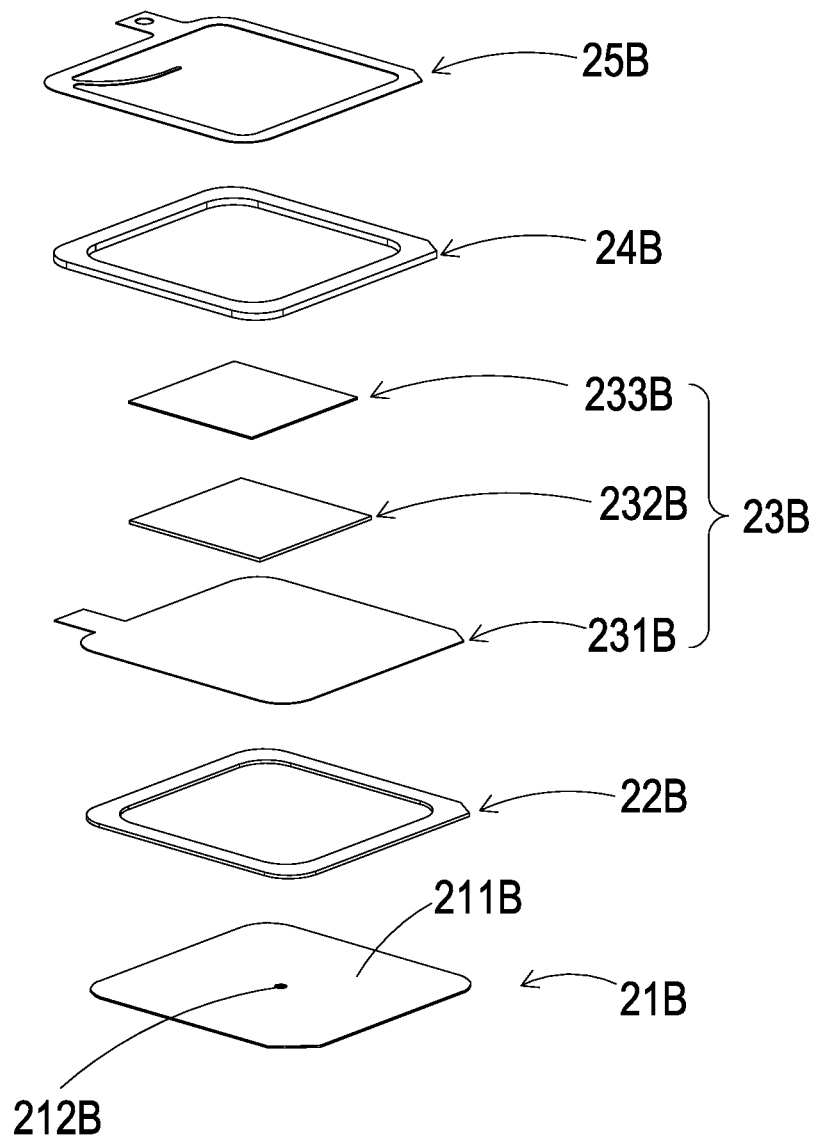
FIG. 5A is a schematic exploded view illustrating the blower-type micro pump of the particle detecting device of the present disclosure and taken along front viewpoint.
Figure 5B:
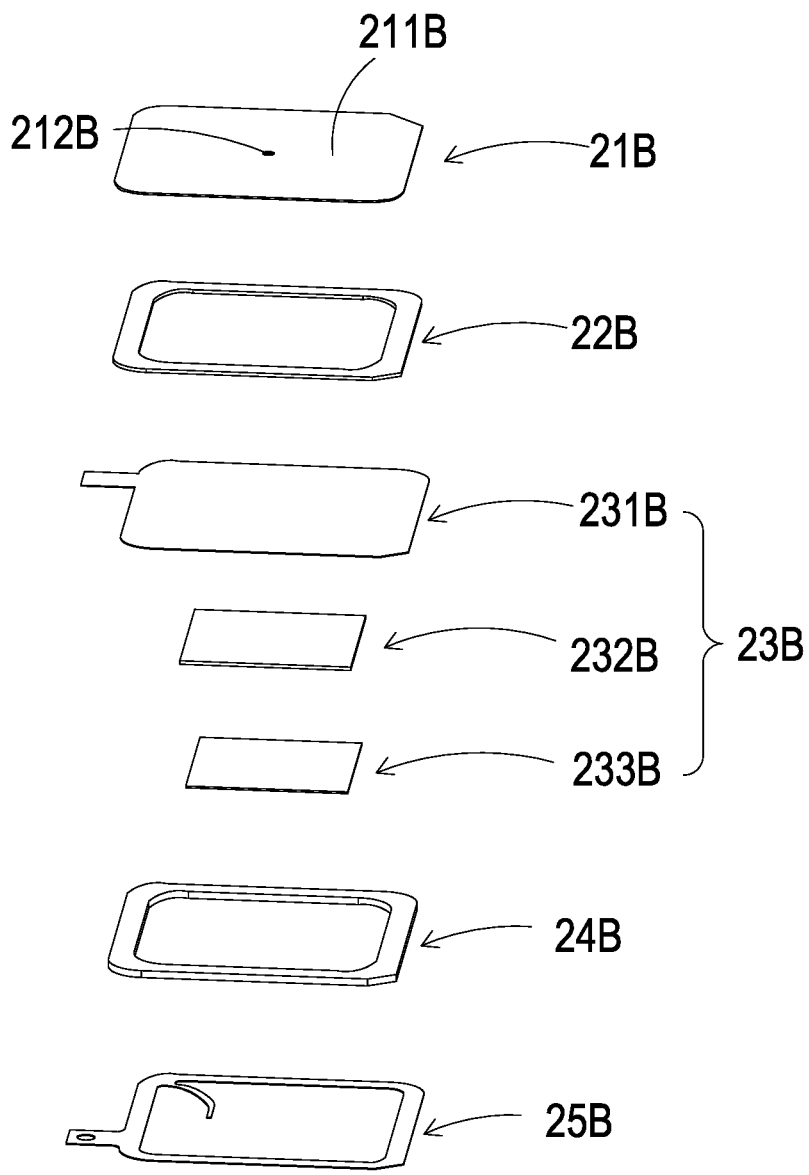
FIG. 5B is a schematic exploded view illustrating the blower-type micro pump of the particle detecting device of the present disclosure and taken along rear viewpoint.

Please refer to FIGS. 5A and 5B. In the embodiment, the blower-type micro pump 2B includes a gas-injection plate 21B, a chamber frame 22B, an actuator element 23B, an insulation frame 24B and a conductive frame 25B. In the embodiment, the gas-injection plate 21B is made by a flexible material and includes a suspension plate 211B and a hollow aperture 212B. The suspension plate 211B permitted to undergo a bending deformation, but not limited thereto. The hollow aperture 212B passes through a center of the suspension plate 211B, so as to allow the gas to flow therethrough. In the embodiment, the chamber frame 22B is carried and stacked on the gas-injection plate 21B. The actuator element 23B is carried and stacked on the chamber frame 22B, and includes a piezoelectric carrying plate 231B, an adjusting resonance plate 232B and a piezoelectric plate 233B. The piezoelectric carrying plate 231B is carried and stacked on the chamber frame 22B. The adjusting resonance plate 232B is carried and stacked on the piezoelectric carrying plate 231B. The piezoelectric plate 233B is carried and stacked on the adjusting resonance plate 232B, so that when a voltage is applied to the piezoelectric plate 233B, the piezoelectric carrying plate 231B and the adjusting resonance plate 232B are driven to generate the bending deformation in the reciprocating manner. In the embodiment, the adjusting resonance plate 232B is located between the piezoelectric plate 233B and the piezoelectric carrying plate 231B and served as a cushion between the piezoelectric plate 233B and the piezoelectric carrying plate 231B. Thereby, the vibration frequency of the piezoelectric carrying plate 231B is adjustable. Basically, the thickness of the adjusting resonance plate 232B is greater than the thickness of the piezoelectric carrying plate 231B, and the thickness of the adjusting resonance plate 232B is adjustable, thereby adjusting the vibration frequency of the actuator element 23B. In the embodiment, the insulation frame 24B is carried and stacked on the actuator element 23B. The conductive frame 25B is carried and stacked on the insulation frame 24B. A resonance chamber 26B is collaboratively defined by the actuator element 23B, the chamber frame 22B and the suspension plate 231B. In that, the gas-injection plate 21B, the chamber frame 22B, the actuator element 23B, the insulation frame 24B and the conductive frame 25B are stacked sequentially. In the embodiment, the gas-injection plate 21B is fixed in a gas-guiding-component carrying seat 27B, and the blower-type micro pump 2B is carried and positioned in the gas-guiding-component carrying seat 27B for supporting and positioning, so that a vacant space 28B is defined between of the suspension plate 211B of the gas-injection plate 21B in the blower-type micro pump 2B and an inner edge of the gas-guiding-component carrying seat 27B for gas to flow therethrough. Moreover, a flowing chamber 29B is formed between the gas-injection plate 21B and the bottom surface of the gas-guiding-component carrying seat 27B. The flowing chamber 29B is in fluid communication with the resonance chamber 26B located between the actuator element 23B, the chamber frame 22B and the suspension plate 211B through the hollow aperture 212B of the gas-injection plate 21B. Through controlling the vibration frequency of the gas in the resonance chamber 26B and making it close to the vibration frequency of the suspension plate 211B, the Helmholtz resonance effect is introduced between the resonance chamber 26B and the suspension plate 211B, thereby improves the efficiency of gas transportation.

Figure 6A:
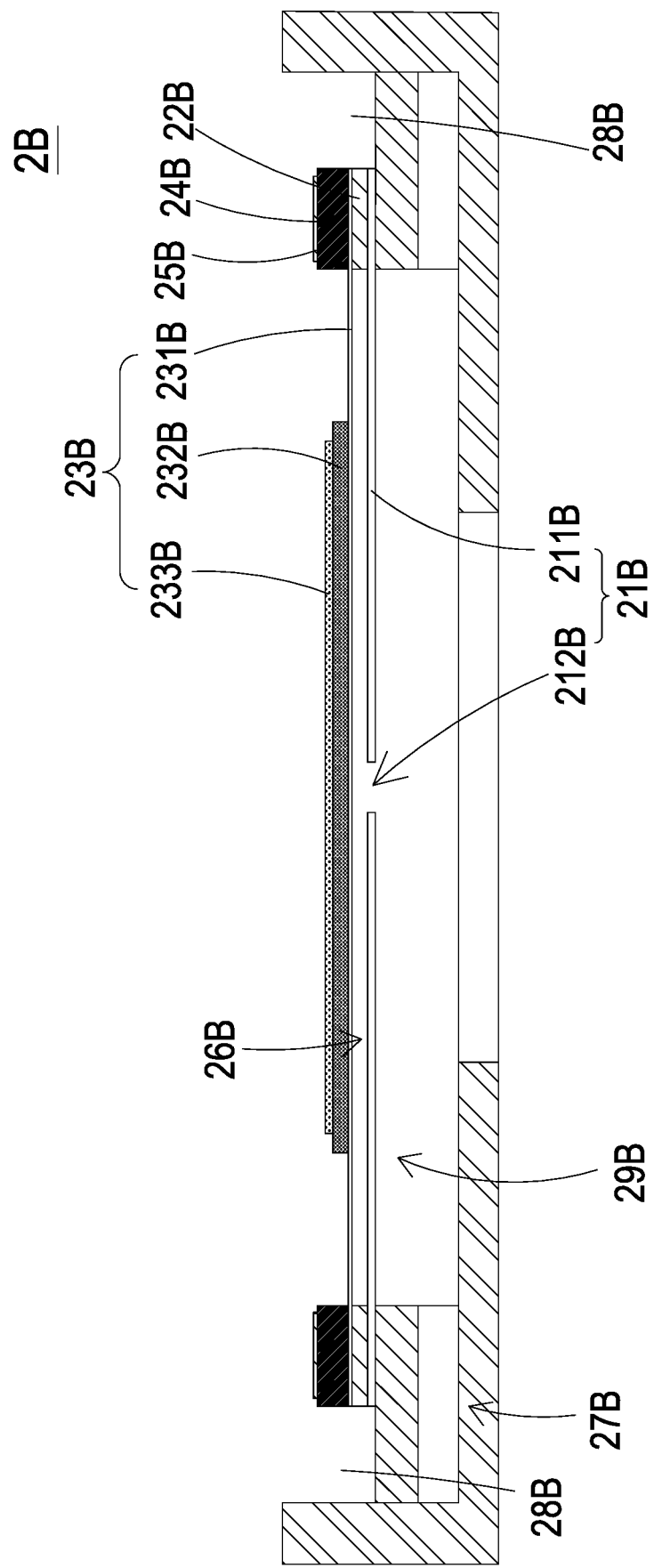
FIG. 6A is a schematic cross-sectional view illustrating the blower-type micro pump of the particle detecting device of the present disclosure.
Figure 6B:
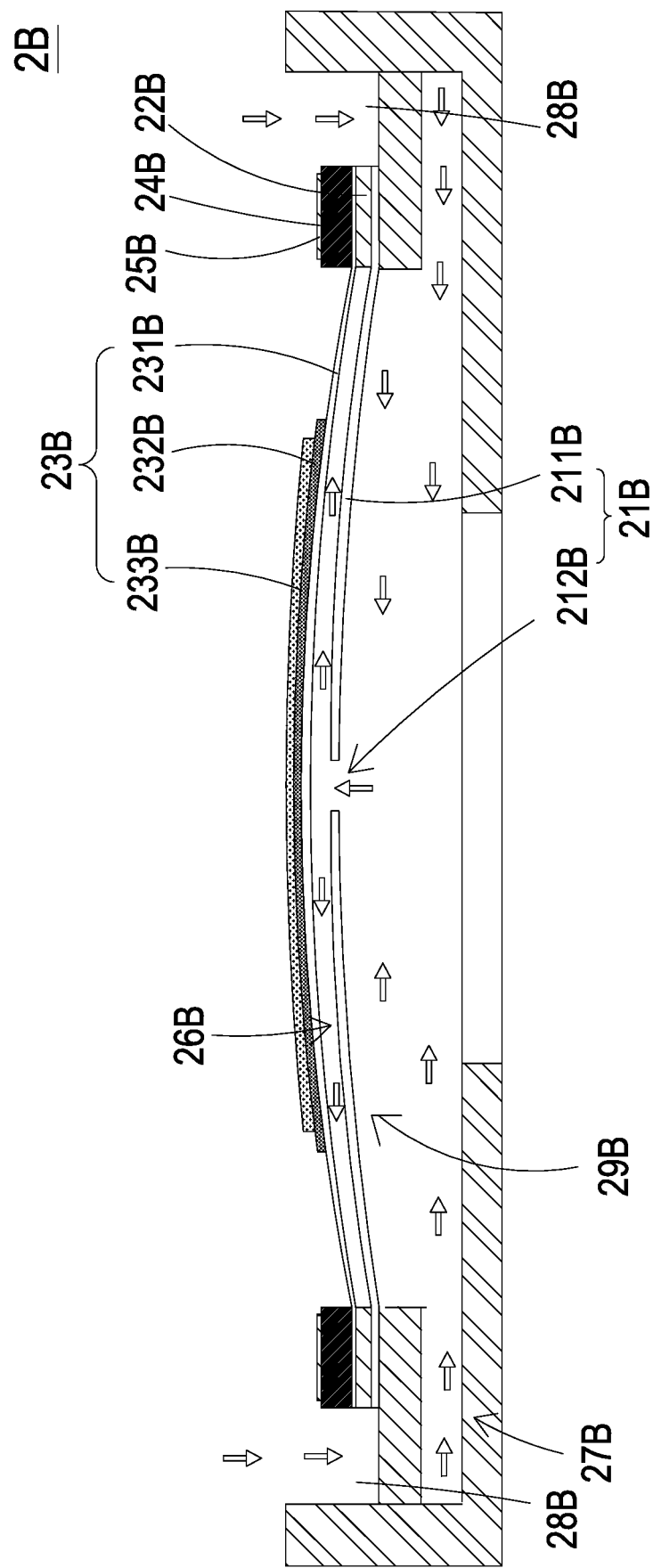
FIGS. 6B to 6C schematically illustrate the operation steps of the blower-type micro pump of FIG. 6A.
Figure 6C:
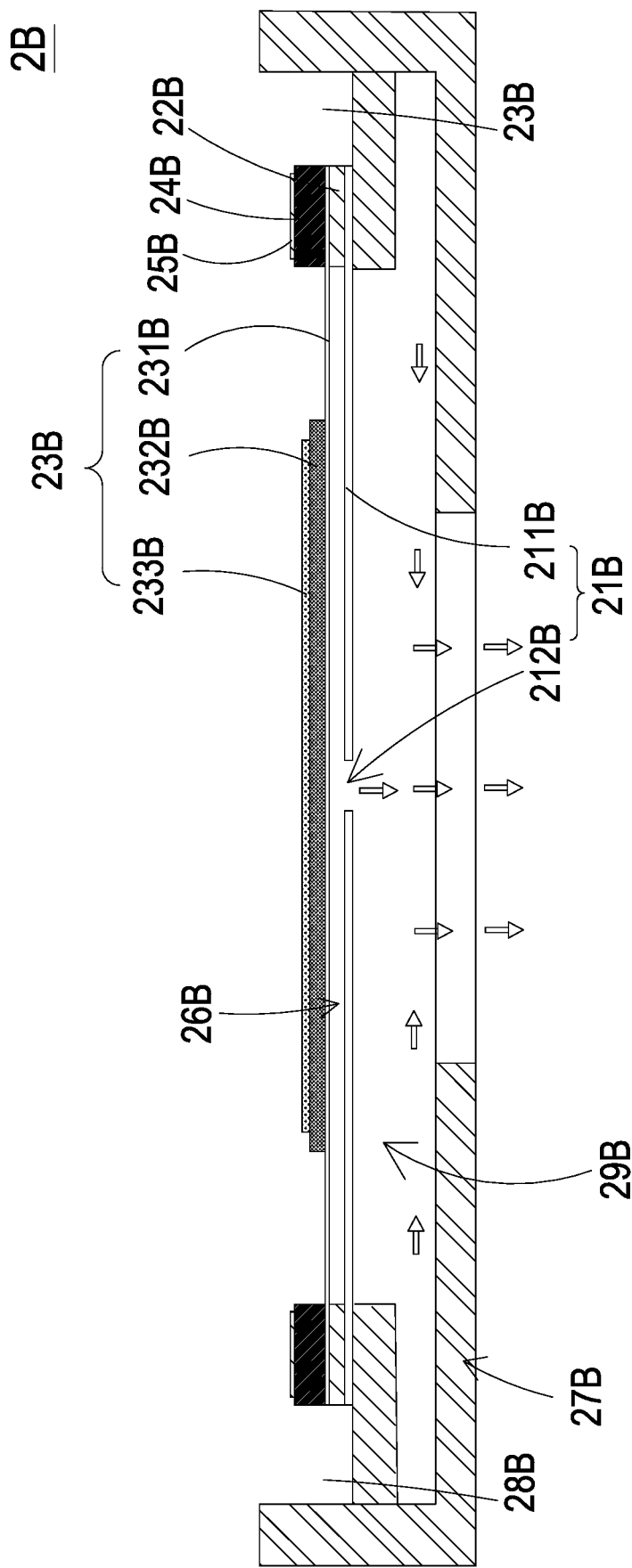

In order to understand the operation steps of the above-mentioned blower-type micro pump 2B for gas transportation, please refer to FIG. 6B. When the piezoelectric plate 233B is moved away from the bottom surface of the gas-guiding-component carrying seat 27B, the suspension plate 211B of the gas-injection plate 21B is driven to move away from the bottom surface of the gas-guiding-component carrying seat 27B by the piezoelectric plate 233B, and the volume of the flowing chamber 29B is expanded rapidly, the internal pressure of the flowing chamber 29B is decreased to generate a negative pressure, and the gas outside the blower-type micro pump 2B is inhaled through the vacant space 28B and enters the resonance chamber 26B through the hollow aperture 212B. Consequently, the pressure in the resonance chamber 26B is increased to generate a pressure gradient. Further as shown in FIG. 6C, when the suspension plate 211B of the gas-injection plate 21B is driven by the piezoelectric plate 233B to move toward the bottom surface of the gas-guiding-component carrying seat 27B, the gas in the resonance chamber 26B is discharged out rapidly through the hollow aperture 212B, and the gas in the flowing chamber 29B is compressed. In that, the converged gas is quickly and massively ejected out of the gas-guiding-component carrying seat 27B in a gas state close to an ideal gas state of the Benulli's law. By repeating the above operation steps shown in FIG. 6B and FIG. 6C, the piezoelectric plate 233B is driven to generate the bending deformation in a reciprocating manner. According to the principle of inertia, the gas pressure inside the resonance chamber 26B after exhausting is lower than the equilibrium gas pressure outside, and the gas is introduced into the resonance chamber 26B again. Moreover, the vibration frequency of the gas in the resonance chamber 26B is controlled to be close to the vibration frequency of the piezoelectric plate 233B, so as to generate the Helmholtz resonance effect and to achieve the gas transportation at high speed and in large quantities.

Figure 7A:
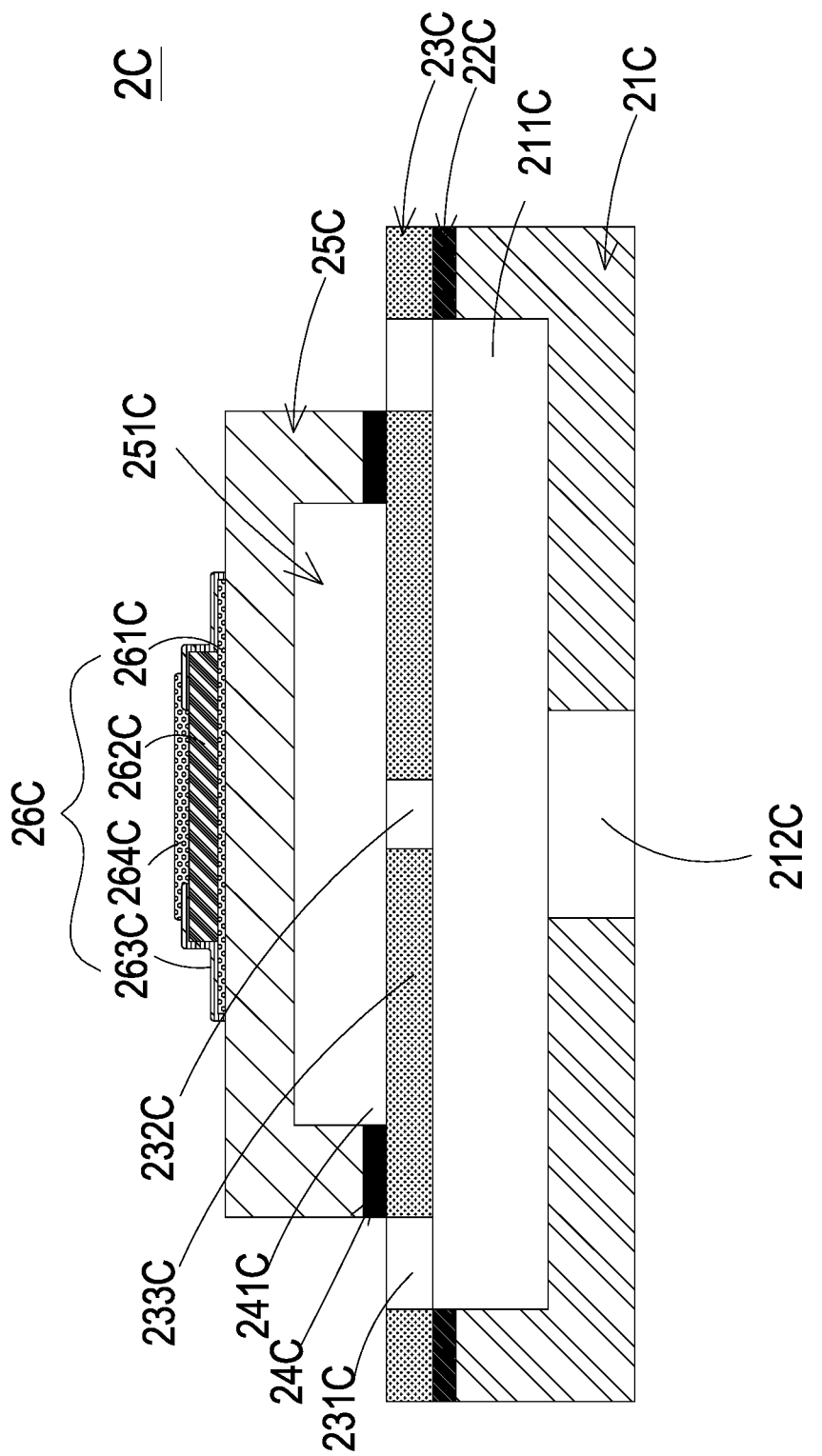
FIG. 7A is a schematic cross-sectional view illustrating the blower-type microelectromechanical-system micro pump of the particle detecting device of the present disclosure.
Figure 7B:
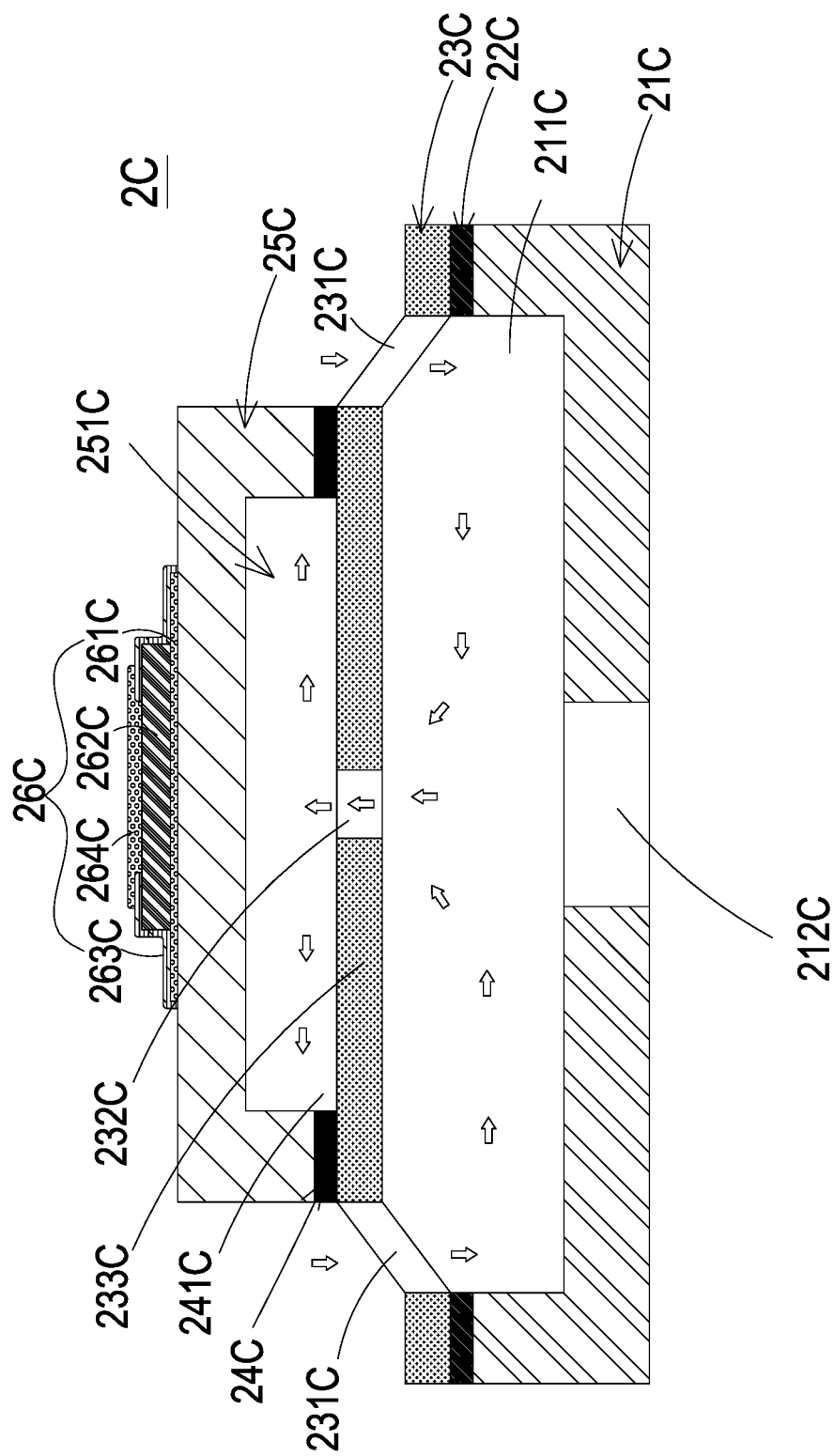
FIGS. 7B to 7C schematically illustrate the operation steps of the blower-type microelectromechanical-system micro pump of FIG. 7A.
Figure 7C:
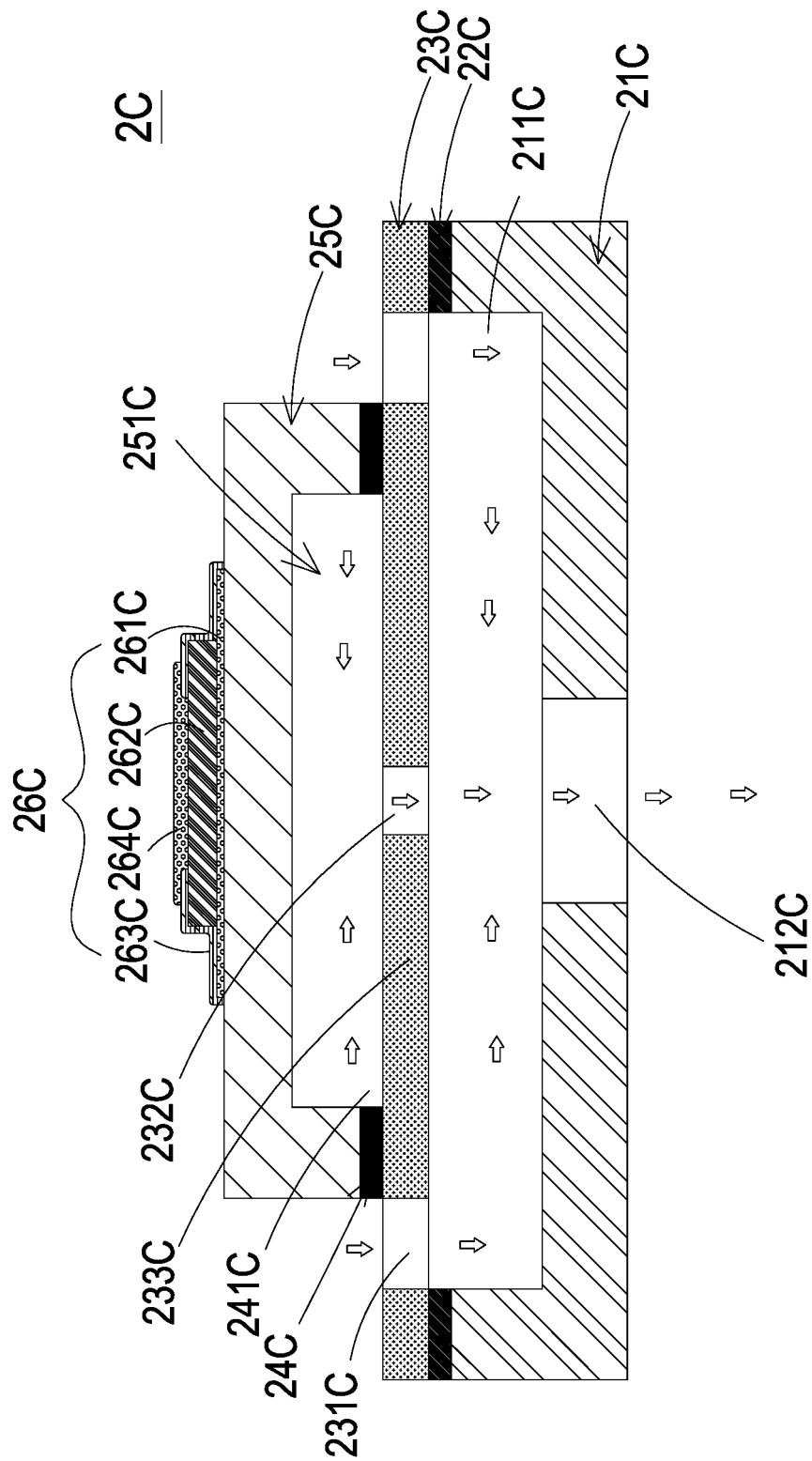

Please refer to FIG. 7A, FIG. 7B and FIG. 7C. In the embodiment, the microelectromechanical-system micro pump 2C includes an outlet base 21C, a first oxidation layer 22C, a gas jetting resonance layer 23C, a second oxidation layer 24C, a resonance-chamber layer 25C and a first piezoelectric component 26C, which are all manufactured by semiconductor process. In the embodiment, the semiconductor process includes at least one etching process and at least one deposition process. The etching process is selected from the group consisting of a wet etching process, a dry etching process and a combination thereof, but not limited thereto. The deposition process is selected from the group consisting of a physical vapor deposition process (PVD), a chemical vapor deposition process (CVD) and a combination thereof, and not redundantly described hereafter.

In the embodiment, the outlet base 21C includes a compression chamber 211C and a through hole 212C manufactured by a silicon-substrate etching process. In the embodiment, the first oxidation layer 22C is formed and stacked on the outlet base 21C by a deposition process, and a part corresponding to the compression chamber 211C is etched to remove. In the embodiment, the gas-jetting resonance layer 23C is formed and stacked on the first oxidation layer 22C by a silicon-substrate deposition process. A plurality of inlet apertures 231C are formed by etching and removing a part corresponding to the compression chamber 211C, and a gas-jetting hole 232C is formed by etching and removing a part corresponding to a center of the compression chamber 211C, so that a suspension section 233C capable of displacing and vibrating is formed between the inlet apertures 231C and the gas jetting hole 232C. In the embodiment, the second oxidation layer 24C is formed and stacked on the suspension section 233C of the gas-jetting resonance layer 23C by a deposition process. A resonance-chamber section 241C is formed by partially etching the second oxidation layer 24C and is in fluid communication with the gas jetting hole 232C. In the embodiment, the resonance-chamber layer 25C includes a resonance chamber 251C formed by a silicon-substrate etching process, and is correspondingly connected and stacked on the second oxidation layer 24C, so that the resonance chamber 251C is corresponding to the resonance-chamber section 241C of the second oxidation 24C. In the embodiment, the first piezoelectric component 26C is formed and stacked on the resonance-chamber layer 25C, and includes a first lower electrode layer 261C, a first piezoelectric layer 262C, a first insulation layer 263C and a first upper electrode layer 264C. The first lower electrode layer 261C is formed and stacked on the resonance-chamber layer 25C by a deposition process. The first piezoelectric layer 262C is formed and stacked on a partial surface of the first lower electrode layer 261C by a deposition process. The first insulation layer 263C is formed and stacked on a partial surface of the first piezoelectric layer 262C by a deposition process. The first upper electrode layer 264C is formed and stacked on the first insulation layer 263C and a remaining surface of the first piezoelectric layer 262C without the first insulation layer 263C disposed thereon by a deposition process, so as to electrically connect with the first piezoelectric layer 262C.

In order to understand the operation steps of the above-mentioned blower-type micro pump 2C for gas transportation, please refer to FIGS. 7B to 7C. When the first piezoelectric component 26C is driven to drive the gas jetting resonance layer 23C and generate a resonance, such that the suspension section 233C of the gas jetting resonance layer 23C is vibrated and displaced in reciprocating manner, whereby a gas is inhaled into the compression chamber 211C through the plurality of inlet apertures 231C, flows through the gas jetting hole 232C and is transported into the resonance chamber 251C. Through controlling the vibration frequency of the gas in the resonance chamber 251C and making it close to the vibration frequency of the suspension section 233C, the Helmholtz resonance effect is introduced between the resonance chamber 251C and the suspension section 233, whereby the gas collected in the resonance chamber 251C is discharged out and transported to the compression chamber 211C, flows through the through hole 212C, and then is discharged out with high pressure, so as to achieve gas transportation under high pressure and improve gas transportation efficiency.

Figure 8A:
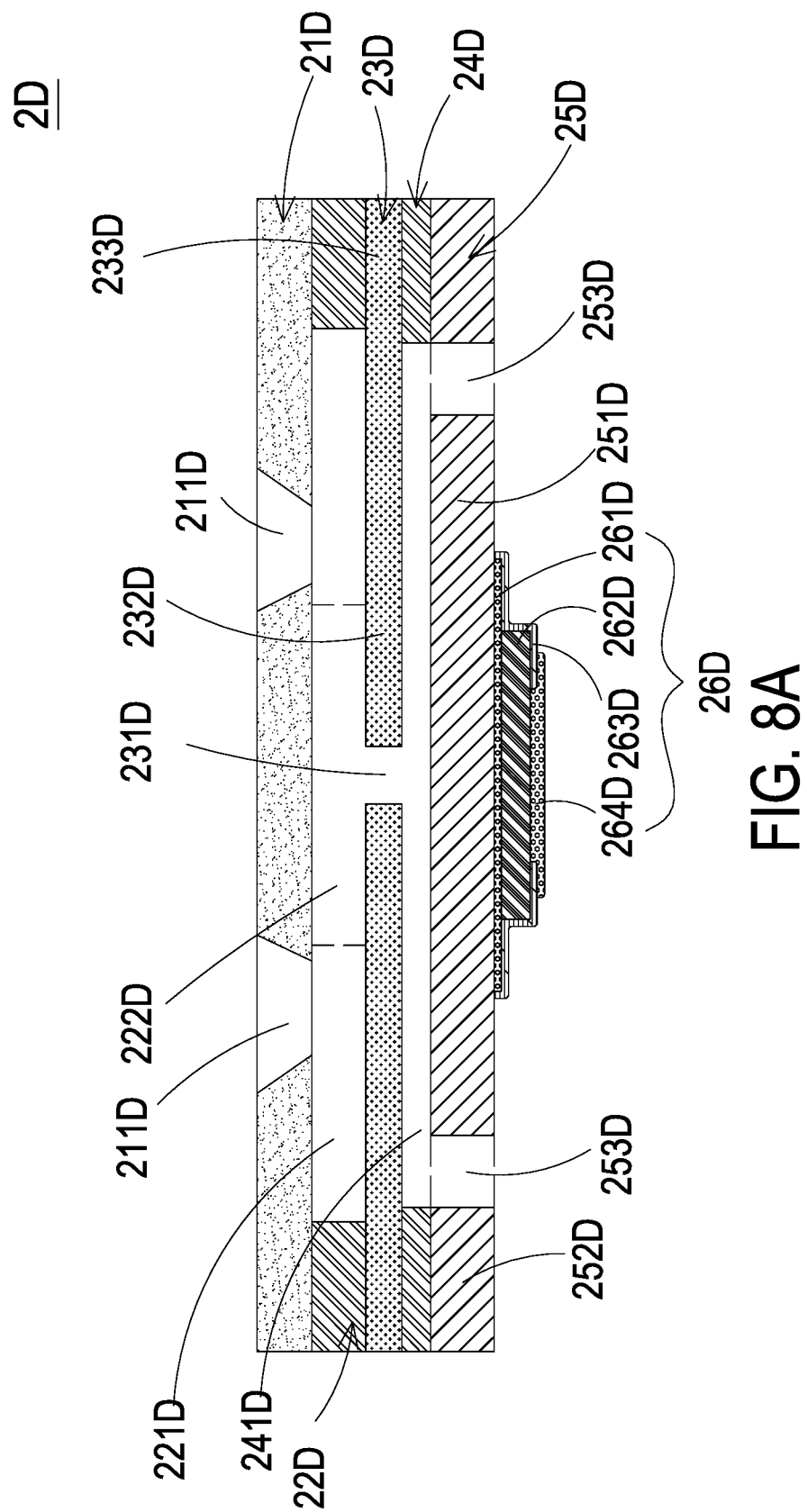
FIG. 8A is a schematic cross-sectional view illustrating the microelectromechanical-system pump of particle detecting device of the present disclosure.
Figure 8B:
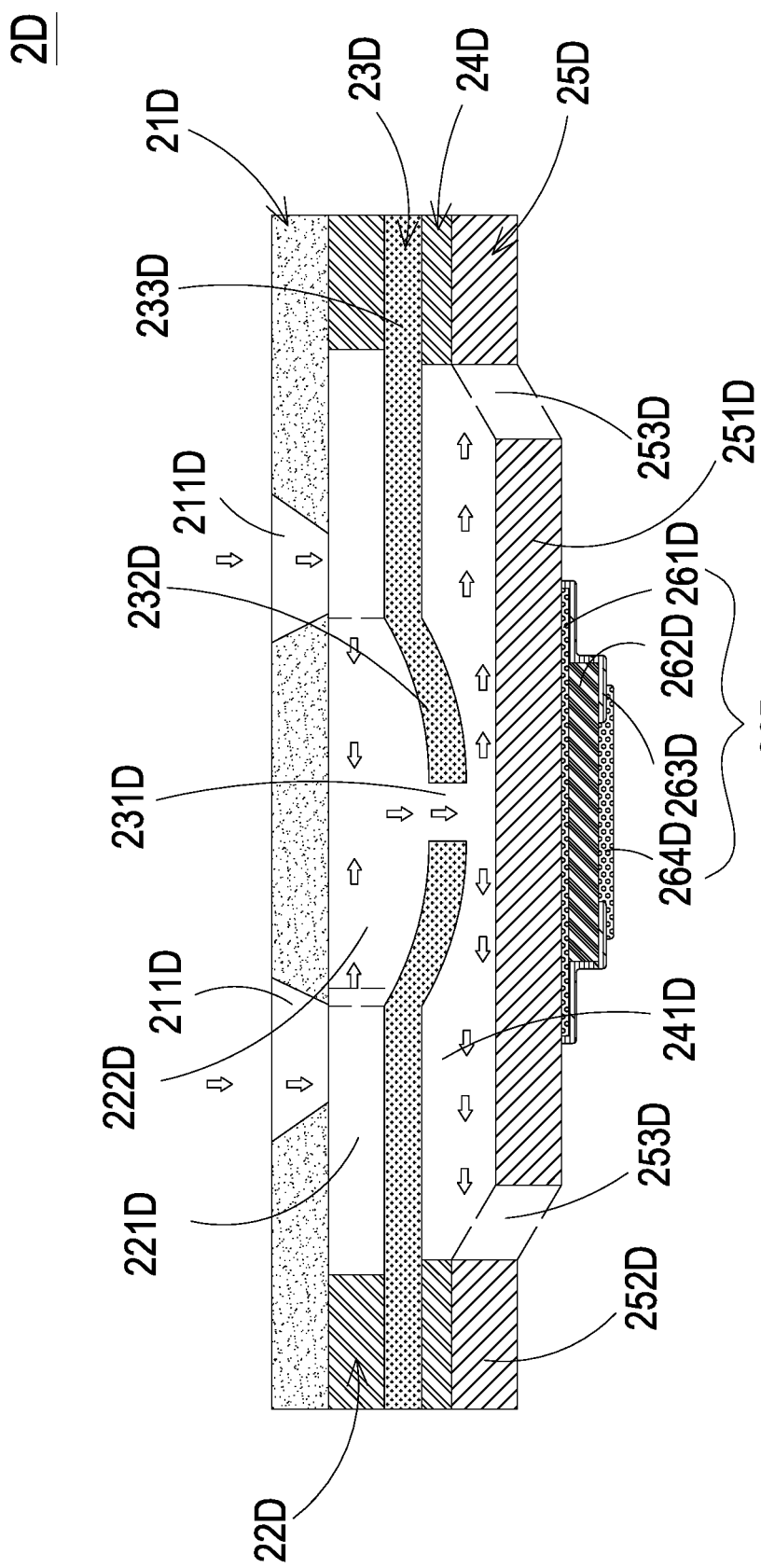
FIGS. 8B to 8C schematically illustrate the operation steps of the microelectromechanical-system pump of FIG. 8A.
Figure 8C:
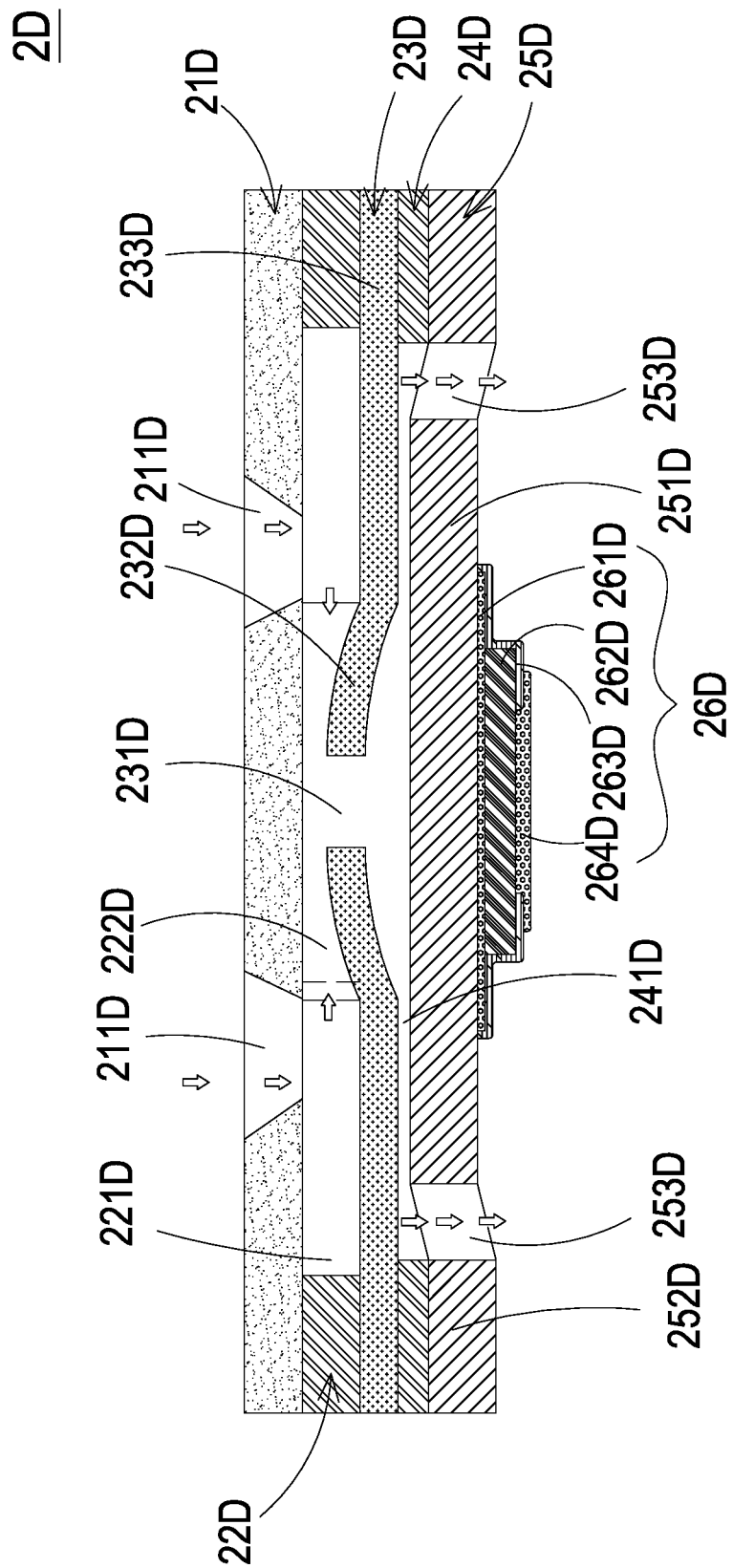

Please refer to FIG. 8A, FIG. 8B and FIG. 8C. In the embodiment, the microelectromechanical-system pump 2D includes an inlet base 21D, a third oxidation layer 22D, a resonance layer 23D, a fourth oxidation layer 24D, a vibration layer 25D and a second piezoelectric component 26D, which are all manufactured by semiconductor process. In the embodiment, the semiconductor process includes at least one etching process and at least one deposition process. The etching process is selected from the group consisting of a wet etching process, a dry etching process and a combination thereof, but not limited thereto. The deposition process is selected from the group consisting of a physical vapor deposition process (PVD), a chemical vapor deposition process (CVD) and a combination thereof, and not redundantly described hereafter.

In the embodiment, the inlet base 21D includes at least one inlet aperture 211D formed by a silicon-substrate etching process. In the embodiment, the third oxidation layer 22D is formed and stacked on the inlet base 21D by a deposition process. The third oxidation layer 22D includes a plurality of convergence channels 221D and a convergence chamber 222D formed by an etching process. The plurality of convergence channels 221D are in fluid communication between the convergence chamber 222D and the at least one inlet aperture 211D of the inlet base 21D. The resonance layer 23D is formed and stacked on the third oxidation layer 22D by a silicon-substrate deposition process, and includes a central through hole 231D, a vibration section 232D and a fixed section 233D formed by an etching process. The central through hole 231D is formed at a center of the resonance layer 23D. The vibration section 232D is disposed around a peripheral region of the central through hole 231D, and the fixed section 233D is disposed around a peripheral region of the resonance layer 23D. The fourth oxidation layer 24D is formed and stacked on the resonance layer 23D by a deposition process, and includes a compression-chamber section 241D formed by etching to partially remove the fourth oxidation layer 24D. In the embodiment, the vibration layer 25D is formed and stacked on the fourth oxidation layer 24D by a silicon-substrate deposition process and includes an actuating section 251D, an outer peripheral section 252D and a plurality of gas apertures 253D formed by an etching process. The actuating section 251D is disposed at a central part of the vibration layer 25D. The outer peripheral section 252D is disposed around an outer periphery of the actuating section 251D, and the plurality of gas apertures 253D are formed between the actuating section 251D and the outer peripheral section 252D, respectively. A compression chamber is collaboratively defined by the vibration layer 25D and the compression-chamber section 241D of the fourth oxidation layer 24D. The second piezoelectric component 26D is formed and stacked on the actuating section 251D of the vibration layer 25D by a deposition process and includes a second lower electrode layer 261D, a second piezoelectric layer 262D, a second insulation layer 263D and a second upper electrode layer 264D. The second layer electrode layer 261D is formed and stacked on the actuating section 251D of the vibration layer 25D by a deposition process. The second piezoelectric layer 262D is formed and stacked on a partial surface of the second lower electrode layer 261D by a deposition process. The second insulation layer 263D is formed and stacked on a partial surface of the second piezoelectric layer 262D by a deposition process. The second upper electrode layer 264D is formed and stacked on the second insulation layer 263D and a remaining surface of the second piezoelectric layer 262D without the second insulation layer 263D disposed thereon by a deposition process, so as to electrically connect with the second piezoelectric layer 262.

In order to understand the operation steps of the above-mentioned the microelectromechanical-system pump 2D for gas transportation, please refer to FIGS. 8B to 8C. When the first piezoelectric component 26D is driven to drive the resonance layer 33D and the vibration layer 35D to displace and generate a resonance effect, the gas introduced from the at least one inlet aperture 211D is converged to the convergence chamber 222D through the plurality of convergence channels 221D, flows through the central through hole 231D of the resonance layer 23, and then is discharged out through the plurality of gas apertures 253D of the vibration layer 25D, so as to achieve gas transportation at high flow.

In summary, the present disclosure provides a portable miniature particle detecting device formed by a resonator and a piezoelectric actuator. The piezoelectric actuator is used to transport a gas into the resonator to allow the resonator to detect a mass and a concentration of the screened and required-diameter particles. Thus, the air quality can be monitored immediately anytime and anywhere, and it allows people to understand the gas quality of the inhaled gas.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A particle detecting device, comprising:
   a resonator comprising a box, a driving board, a piezoelectric vibrator and a suspended-particle sensor, wherein the box comprises a sampling chamber, an air inlet and a waterproof and breathable membrane, the air inlet is covered and attached by the waterproof and breathable membrane for filtering large particles with a particle size large than or equal to a threshold diameter contained in an external gas, so that screened and required-diameter particles with particle size smaller than the threshold diameter can pass through the waterproof and breathable membrane and be inhaled into the sampling chamber, and the driving board is disposed on bottom of the sampling chamber and comprises at least one passage hole disposed thereon, the piezoelectric vibrator is packaged on the driving board, wherein the suspended-particle sensor is packaged on the piezoelectric vibrator, and the suspended-particle sensor corresponds to the air inlet and maintains a spacing distance, wherein the driving board provides driving power and operation frequency to the piezoelectric vibrator to change a resonance frequency of the piezoelectric, and the screened and required-diameter particles are sedimented and collected on a surface of the suspended-particle sensor, so that a mass and a concentration of the screened and required-diameter particles can be detected; and
   a piezoelectric actuator disposed on, sealed and connected to one side of the resonator, so that the external gas is inhaled into the sampling chamber through the air inlet, flows and passes by the suspended-particle sensor, and is discharged out of the particle detecting device through the at least one passage hole and the piezoelectric actuator in sequence.

2. The particle detecting device according to claim 1, wherein the piezoelectric actuator is a micro pump, and the micro pump comprises:
   an inlet plate comprising at least one inlet aperture, at least one convergence channel and a convergence chamber, wherein the at least one inlet aperture is disposed to inhale the gas, the at least one convergence channel is disposed corresponding in position to the inlet aperture, and the convergence channel is in communication with the inlet aperture and convergence to the convergence chamber, so as to guide the gas inhaled from the inlet aperture to the convergence chamber;
   a resonance plate attached on the inlet plate and having a central aperture, a movable part and a fixed part, wherein the central aperture is disposed at a center of the resonance plate, and is corresponding in position to the convergence chamber of the inlet plate, the movable part surrounds the central aperture and is corresponding in position to the convergence chamber, and the fixed part surrounded the movable part is fixedly attached on the inlet plate; and
   a piezoelectric member attached on the resonance plate, corresponding in position to the resonance plate, and comprising a suspension plate, an outer frame, at least one bracket and a piezoelectric element, wherein the suspension plate is square-shaped and permitted to undergo a bending deformation, the outer frame is disposed around a periphery of the suspension plate, the at least one bracket is connected between the suspension plate and the outer frame for elastically supporting the suspension plate, and the piezoelectric element is attached to a surface of the suspension plate for driving the suspension plate to undergo the bending deformation as a voltage is applied thereto;

wherein a chamber space is formed between the resonance plate and the piezoelectric member, wherein when the piezoelectric member is driven, the gas introduced from the at least one inlet aperture of the inlet plate is converged to the convergence chamber through the at least one convergence channel, and flows through the central aperture of the resonance plate, whereby a resonance effect is generated by the piezoelectric member and the movable part of the resonance plate to transport the gas.

3. The particle detecting device according to claim 2, wherein the micro pump further comprises a first insulation plate, a conductive plate and a second insulation plate, wherein the inlet plate, the resonance plate, the piezoelectric member, the first insulation plate, the conductive plate and the second insulation plate are stacked sequentially.

4. The particle detecting device according to claim 1, wherein the piezoelectric actuator is a blower-type micro pump, the blower-type micro pump is fixed in a gas-guiding-component carrying seat, and the blower-type micro pump comprises:

a gas-injection plate fixed in the gas-guiding-component carrying seat and comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element carried and stacked on the chamber frame, and comprising a piezoelectric carrying plate, an adjusting resonance plate and a piezoelectric plate, wherein the piezoelectric carrying plate is carried and stacked on the chamber frame, the adjusting resonance plate is carried and stacked on the piezoelectric carrying plate, and the piezoelectric plate is carried and stacked on the adjusting resonance plate, wherein the piezoelectric plate is configured to drive the piezoelectric carrying plate and the adjusting resonance plate to generate the bending deformation in the reciprocating manner as a voltage is applied thereto;

an insulation frame carried and stacked on the actuator element; and a conductive frame carried and stacked on the insulation frame;

wherein the gas-injection plate is fixed in the gas-guiding-component carrying seat for supporting and positioning, so that a vacant space is defined between the gas-injection plate and an inner edge of the gas-guiding-component carrying seat for gas to flow therethrough, a flowing chamber is defined between the gas-injection plate and a bottom of the gas-guiding-component carrying seat, and a resonance chamber is formed between the actuator element, the chamber frame and the suspension plate, wherein when the actuator element is enabled to drive the gas-injection plate to move in resonance therewith, the suspension plate of the gas-injection plate is driven to generate the bending deformation in a reciprocating manner, the gas is inhaled through the vacant space, flows into the flowing chamber, and is discharged out, so as to achieve gas transportation.

5. The particle detecting device according to claim 1, wherein the piezoelectric actuator is a blower-type microelectromechanical-system micro pump and the blower-type microelectromechanical-system micro pump comprises:

an outlet base comprising a compression chamber and a through hole formed by a silicon-substrate etching process;

a first oxidation layer formed and stacked on the outlet base by a deposition process, wherein a part corresponding to the compression chamber is etched to remove;

a gas jetting resonance layer formed and stacked on the first oxidation layer by a silicon-substrate deposition process, wherein a plurality of inlet apertures are formed by etching and removing a part of the gas jetting resonance layer corresponding to the compression chamber, and a gas jetting hole is formed by etching and removing a part of the gas jetting resonance layer corresponding to a center of the compression chamber, so that a suspension section capable of displacing and vibrating is formed between the inlet apertures and the gas jetting hole;

a second oxidation layer formed and stacked on the suspension section of the gas-jetting resonance layer by a deposition process, wherein a resonance-chamber section is formed by partially etching the second oxidation layer and is in fluid communication with the gas jetting hole;

a resonance-chamber layer comprising a resonance chamber formed by a silicon-substrate etching process, and is correspondingly connected and stacked on the second oxidation layer, so that the resonance chamber is corresponding to the resonance-chamber section of the second oxidation; and a first piezoelectric component formed and stacked on the resonance-chamber layer, and comprising a first lower electrode layer, a first piezoelectric layer, a first insulation layer and a first upper electrode layer, wherein the first lower electrode layer is formed and stacked on the resonance-chamber layer by a deposition process, the first piezoelectric layer is formed and stacked on a partial surface of the first lower electrode layer by a deposition process, the first insulation layer is formed and stacked on a partial surface of the first piezoelectric layer by a deposition process, and the first upper electrode layer is formed and stacked on the first insulation layer and a remaining surface of the first piezoelectric layer without the first insulation layer disposed thereon by a deposition process, so as to electrically connect with the first piezoelectric layer;

wherein when the first piezoelectric component is driven to drive the gas jetting resonance layer and generate a resonance effect, the suspension section of the gas jetting resonance layer is vibrated and replaced in reciprocating manner, whereby the gas is inhaled into the compression chamber through the plurality of inlet apertures, flows through the gas jetting hole and is transported into the resonance chamber, wherein the gas collected in the resonance chamber is discharged out and transported to the compression chamber, flows through the through hole, and then is discharged out from the outlet chamber under high pressure, so as to achieve gas transportation.

6. The particle detecting device according to claim 1, wherein the piezoelectric actuator is a microelectromechanical-system micro pump and the microelectromechanical-system micro pump comprises:

> an inlet base comprising at least one inlet aperture formed by a silicon-substrate etching process;
>
> a third oxidation layer formed and stacked on the inlet base by a deposition process, wherein the third oxidation layer comprises a plurality of convergence channels and a convergence chamber formed by an etching process, and the plurality of convergence channels are in fluid communication between the convergence chamber and the at least one inlet aperture of the inlet base;
>
> a resonance layer formed and stacked on the third oxidation layer by a silicon-substrate deposition process, and comprising a central through hole, a vibration section and a fixed section formed by an etching process, wherein the central through hole is formed at a center of the resonance layer, the vibration section is disposed around a peripheral region of the central through hole, and the fixed section is disposed around a peripheral region of the resonance layer;
>
> a fourth oxidation layer formed and stacked on the resonance layer by a deposition process, and comprising a compression-chamber section formed by etching to partially remove the fourth oxidation layer;
>
> a vibration layer formed and stacked on the fourth oxidation layer by a silicon-substrate deposition process and comprising an actuating section, an outer peripheral section and a plurality of gas apertures formed by an etching process, wherein the actuating section is disposed at a central part of the vibration layer, the outer peripheral section is disposed around an outer periphery of the actuating section, and the plurality of gas apertures are formed between the actuating section and the outer peripheral section, respectively, wherein a compression chamber is collaboratively defined by the vibration layer and the compression-chamber section of the fourth oxidation layer; and
>
> a second piezoelectric component formed and stacked on the actuating section of the vibration layer by a deposition process and comprising a second lower electrode layer, a second piezoelectric layer, a second insulation layer and a second upper electrode layer, wherein the second layer electrode layer is formed and stacked on the actuating section of the vibration layer by a deposition process, the second piezoelectric layer is formed and stacked on a partial surface of the second lower electrode layer by a deposition process, the second insulation layer is formed and stacked on a partial surface of the second piezoelectric layer by a deposition process, and the second upper electrode layer is formed and stacked on the second insulation layer and a remaining surface of the second piezoelectric layer without the second insulation layer disposed thereon by a deposition process, so as to electrically connect with the second piezoelectric layer;
>
> wherein when the second piezoelectric component is driven to drive the vibration layer and generate a resonance displacement of the resonance layer, and the gas introduced from the at least one inlet aperture is converged to the convergence chamber through the plurality of convergence channels, flows through the central through hole of the resonance layer, and then is discharged out through the plurality of gas apertures of the vibration layer, so as to achieve gas transportation.

7. The particle detecting device according to claim 1, wherein the piezoelectric vibrator is a quartz chip.

8. The particle detecting device according to claim 1, wherein the suspended-particle sensor is one of a PM10 sensor, a PM2.5 sensor, or a PM1 sensor.

9. The particle detecting device according to claim 1, wherein the threshold diameter is 10 μm.

* * * * *